United States Patent

Grossmann et al.

Patent Number: 5,087,282
Date of Patent: Feb. 11, 1992

[54] SULFONYLURA AGENTS FOR DEFOLIATING COTTON

[75] Inventors: Klaus Grossmann, Limburgerhof; Gerhard Hamprecht, Weinheim; Bruno Wuerzer, Otterstadt, all of Fed. Rep. of Germany

[73] Assignee: BASF Aktiengesellschaft, Ludwigshafen, Fed. Rep. of Germany

[21] Appl. No.: 561,615

[22] Filed: Aug. 2, 1990

[30] Foreign Application Priority Data

Aug. 7, 1989 [DE] Fed. Rep. of Germany ........ 3926056

[51] Int. Cl.⁵ .................................................. A01N 31/08
[52] U.S. Cl. ........................................... 71/72; 71/73; 71/74; 71/93; 71/103; 71/119
[58] Field of Search .................................. 71/73, 93, 72

[56] References Cited

U.S. PATENT DOCUMENTS 4,127,405 11/1978 Levitt .................................. 71/93
4,659,366 4/1987 Stetter et al. ....................... 71/92

FOREIGN PATENT DOCUMENTS 0007687 2/1980 European Pat. Off. .
0136061 4/1985 European Pat. Off. .
0291851 5/1988 European Pat. Off. .
0318620 6/1989 European Pat. Off. .
3413490 10/1985 Fed. Rep. of Germany .
3413565 10/1985 Fed. Rep. of Germany .

Primary Examiner—Richard L. Raymond
Assistant Examiner—S. Mark Clardy
Attorney, Agent, or Firm—Keil & Weinkauf

[57] ABSTRACT

Agents for defoliating cotton plants contain, in addition to conventional additives, a phenylsulfonyl- or hetarylsulfonylurea I

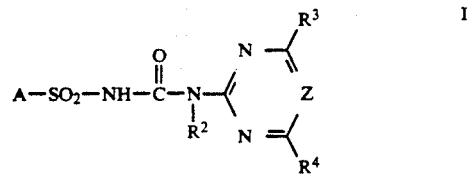

where A is substituted phenyl, benzyl or a heteroaromatic radical,
Rhu 2 is hydrogen or methyl,
$R^3$ is methyl, methoxy, difluoromethoxy, chlorine or methylamino,
$R^4$ is methyl, methoxy, difluoromethoxy or ethoxy and
Z is CH or N, or an alkali metal or alkaline earth metal salt of the compounds I.

7 Claims, No Drawings

SULFONYLURA AGENTS FOR DEFOLIATING COTTON

The present invention relates to agents for defoliating cotton plants, containing, in addition to conventional additives, a phenylsulfonyl- or hetarylsulfonylurea of the general formula I

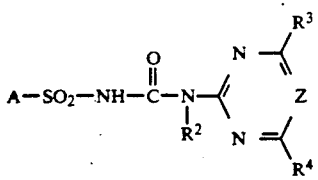

where A is an aromatic or heteroaromatic radical of the structures A-1 to A-5

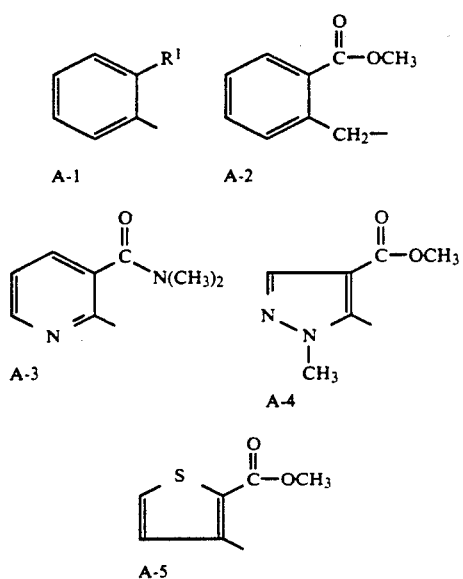

in which $R^1$ is chlorine, carbomethoxy, carboethoxy, 2-chloroethoxy or 2-methoxyethoxy, $R^2$ is hydrogen or methyl, $R^3$ is methyl, methoxy, difluoromethoxy, chlorine or methylamino, $R^4$ is methyl, methoxy, difluoromethoxy or ethoxy and Z is CH or N, or the alkali metal or alkaline earth metal salts of the compound I.

The present invention furthermore relates to an agent for defoliating cotton plants, containing, in addition to conventional additives, a phenylsulfonyl- or hetarylsulfonylurea I or an alkali metal or alkaline earth metal salt thereof and, as a synergistic agent, a compound from the group consisting of the N-phenyl-3,4,5,6-tetrahydrophthalimides (II).

DE-A 3 413 565 discloses the defoliant effect of substituted phenylsulfonylureas on cotton. The example mentioned also clearly reveals that the falling of the leaves is accompanied by simultaneous drying out of the leaves.

U.S. Pat. No. 4,127,405 describes the herbicidal action of phenylsulfonylureas whose phenyl ring is unsubstituted or substituted by fluorine atoms in the ortho-position to the sulfonyl group on bush beans, a defoliant effect being described as an accompanying symptom of the action. However, the defoliant effect on cotton plants is unsatisfactory.

Furthermore, EP-A 0 291 851 and EP-A 136 061 describe phenylsulfonylureas having an alkoxycarbonyl group in the ortho-position to the sulfonyl group. However, only their herbicidal and growth-regulating action is described there. A defoliant effect is not mentioned.

EP-A 0 318 620 discloses phenylsulfonylureas having an alkoxycarbonyl group in the ortho-position to the sulfonyl group and possessing a heteroaliphatic radical in the meta-position. However, only herbicidal and growth-regulating properties are described for these substances; they have a growth-inhibiting effect on cotton.

Phenylsulfonylureas having, in the ortho-position to the sulfonyl group, an alkoxycarbonyl group whose alkoxy moiety carries an oxime radical are disclosed in DE-A 34 13 490. Although the possible use of these compounds as defoliants is pointed out, their good tolerance by crops and therefore possible use as herbicides in cotton crops is specially singled out.

EP-A 7687 discloses the defoliant effect on bush beans of phenylsulfonylureas which carry an alkoxycarbonyl radical in the ortho-position to the sulfonyl group. For young cotton plants, no defoliant effect but merely a herbicidal action is found.

Hetarylsulfonylureas are described in Patent Applications EP-A 237 292 and EP-A 30 142 and U.S. Pat. No. 4,127,405 for use as herbicides, an accompanying defoliant effect on bush beans being found in some cases.

It is also known that, in general, the biological action of the sulfonylureas is very slow to begin. Proc. Br. Crop. Prot. Conf. Weeds 1980, I 7-14 states that, in the case of treatment with the sulfonylurea Glean ®, the herbicidal effect or the dying of sensitive plants takes place slowly and is accompanied by chloroses, necroses, the dying of shoots and decoloration of the leaf nerves.

N-Phenyl-3,4,5,6-tetrahydrophthalimides for the desiccation and abscission of plant organs are described in DE-A 39 05 916.

There is considerable commercial interest in both abscission agents and desiccants for facilitating harvesting. Particularly in intensive cotton cultivation, the use of defoliants is a basic requirement for effective use of plucking machines for harvesting the bolls. For reasons relating to harvesting, defoliation in the form of green leaf parts is preferred in this case to pure desiccation and withering of the remaining plants, since otherwise the fiber quality is very adversely affected by soiling due to withered leaf residues. Furthermore, the defoliants used to date do not satisfactorily prevent resprouting of the leaves. Moreover, commercial organophosphorus compounds have an annoying odor and only limited environmental compatibility. In addition, temperature dependence of the defoliant effect, as occurs in the case of N-phenyl-N'-(1,2,3-thiazol-5-yl)-urea, is undesirable.

It is an object of the present invention to provide novel and better defoliants, especially for cotton.

We have found that this object is achieved by the agents, defined at the outset, for defoliating cotton.

Particularly preferred compounds I are those in which the substituents have the following meanings: A is a phenyl radical A-1 substituted by $R^1$, $R^2$ is hydrogen, $R^3$ is chlorine, methyl or methoxy, R is methyl or methoxy and Z is CH or N, or the sulfonylurea in which A is the group A-5, $R^2$ is hydrogen, $R^3$ is methyl, $R^4$ is methoxy and Z is N.

Examples are the commercial products stated in Tables 1 and 2 below

TABLE 1

Phenylsulfonylureas Ia (where A = A-1)

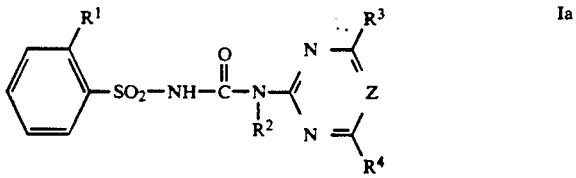

| Comp. No. | $R^1$ | $R^2$ | $R^3$ | $R^4$ | Z | disclosed in |
|---|---|---|---|---|---|---|
| 1 | Cl | H | $CH_3$ | $OCH_3$ | N | DE-A 27 15 786 |
| 2 | $COOCH_3$ | H | $CH_3$ | $OCH_3$ | N | EP-A 7687 |
| 3 | $COOCH_3$ | $CH_3$ | $CH_3$ | $OCH_3$ | N | EP-A 202 830 |
| 4 | $OCH_2CH_2Cl$ | H | $CH_3$ | $OCH_3$ | N | EP-A 44 808 |
| 5 | $OCH_2CH_2OCH_3$ | H | $OCH_3$ | $OCH_3$ | N | EP-A 44 807 |
| 6 | $COOCH_3$ | H | $NHCH_3$ | $OC_2H_5$ | N | EP-A 136 061 |
| 7 | $COOCH_3$ | H | $CH_3$ | $CH_3$ | CH | EP-A 7687 |
| 8 | $COOC_2H_5$ | H | Cl | $OCH_3$ | CH | US-A 4 547 215 |
| 9 | $COOCH_3$ | H | $OCHF_2$ | $OCHF_2$ | CH | EP-A 84 020 |

TABLE 2

Hetarylsulfonylureas Ib (where A = A-2 to A-5 and $R^2$ = H)

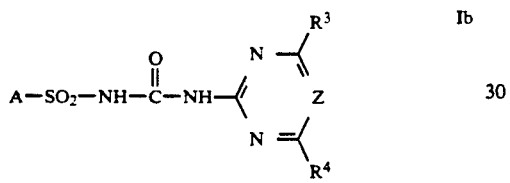

| Comp. No. | A | $R^3$ | $R^4$ | Z | disclosed in |
|---|---|---|---|---|---|
| 10 | A-5 | $CH_3$ | $OCH_3$ | N | EP-A 30 142 |
| 11 | A-3 | $OCH_3$ | $OCH_3$ | CH | EP-A 237 292 |
|  |  |  |  |  | EP-A 232 067 |
| 12 | A-4 | $OCH_3$ | $OCH_3$ | CH | JP 59-219 281 pub. 20.04.83 |
|  |  |  |  |  | CA 102, 220 905 |
| 13 | A-2 | $OCH_3$ | $OCH_3$ | CH | EP-A 51 466 |

The commercial products stated in Tables 1 and 2 are known, for example, under the commercial names Glean ®, Ally ®, Express ®, Logran ®, Setoff ®, Muster ®, Londax ®, Oust ®, Classic ®, Beacon ®, Harmony ® or Remedy ®. They can be prepared by the methods stated in the literature cited.

Compounds I have acidic properties, since the proton on the nitrogen atom present between the sulfonyl and the carbonyl group can readily be eliminated. With bases, the corresponding basic salts are therefore obtained. Examples of suitable bases are alkali metal or alkaline earth metal hydroxides, such as sodium hydroxide or potassium hydroxide, or alkali metal or alkaline earth metal alcoholates. Sodium methylate or potassium methylate is preferably used.

The phenylsulfonyl- or hetarylsulfonylureas I are suitable as defoliants for cotton plants before harvesting of the bolls. They act at very low application rates and effectively prevent the growth of new shoots. In the mode of action, defoliation of green, turgescent leaves predominates over the desiccation effect and thus helps to achieve higher fiber quality.

The phenylsulfonyl- or hetarylsulfonylureas I can be used, for example, in the form of directly sprayable solutions, powders, suspensions, including concentrated aqueous, oily or other suspensions or dispersions, emulsions, oil dispersions, pastes, dusts, broadcasting agents or granules, by spraying, atomizing, dusting, broadcasting or pouring. The application forms depend entirely on the intended uses; they should in any case ensure very fine distribution of the active ingredients.

Mineral oil fractions having a medium to high boiling point, such as kerosene or diesel oil, coal tar oils and oils of vegetable or animal origin, aliphatic, cyclic and aromatic hydrocarbons, e.g. benzene, toluene, xylene, paraffin, tetrahydronaphthalene, alkylated naphthalenes or derivatives thereof, for example methanol, ethanol, propanol, butanol, chloroform, carbon tetrachloride, cyclohexanol, cyclohexanone, chlorobenzene or isophorone, or strongly polar solvents, such as dimethylformamide, dimethyl sulfoxide, N-methylpyrrolidone or water, are suitable for the preparation of directly sprayable solutions, emulsions, pastes or oil dispersions.

Aqueous application forms can be prepared from emulsion concentrates, pastes or wettable powders (spray powders, oil dispersions) by adding water. For the preparation of emulsions, pastes or oil dispersions, the substances as such, dissolved in an oil or solvent, can be homogenized in water by means of wetting agents, adhesives, dispersants or emulsifiers. However, concentrates which consist of active substance, wetting agents, adhesives, dispersants or emulsifiers and possibly solvents or oil and which are suitable for dilution with water can also be prepared.

Suitable surfactants are alkali metal, alkaline earth metal and ammonium salts of ligninsulfonic acid, naphthalenesulfonic acid, phenylsulfonic acid, alkylarylsulfonates, alkyl sulfates, alkylsulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, octadecanols, salts of sulfated fatty alcohol glycol ethers, condensates of sulfonated naphthalene and naphthalene derivatives with formaldehyde, condensates of naphthalene or of naphthalenesulfonic acid with phenol and formaldehyde, polyoxyethylene octylphenol ethers, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methylcellulose.

Powder, broadcasting, coated, impregnated and homogeneous granules can be prepared by binding the active ingredients to solid carriers. Solid carriers are mineral earths, such as silica gel, silicas, silicates, talc, kaolin, attaclay, limestone, lime, chalk, bole, loess, clay, dolomite, kieselguhr, calcium sulfate, magnesium sulfate, magnesium oxide, milled plastics, fertilizers, eg. ammonium sulfate, ammonium phosphate, ammonium nitrate, ureas and plant products, such as cereal meal, ground bark, woodmeal and nutshell meal, cellulose powder and other solid carriers.

The formulations contain from 0.1 to 95, preferably from 0.5 to 90% by weight of active ingredient.

Examples of formulations are:

I. 90 parts by weight of compound No. 1 are mixed with 10 parts by weight of N-methyl-α-pyrrolidone and a solution which is suitable for use in the form of very small drops is obtained.

II. 20 parts by weight of compound No. 2 are dissolved in a mixture which consists of 80 parts by weight of xylene, 10 parts by weight of the adduct of from 8 to 10 moles of ethylene oxide with 1 mole of oleic acid N-monoethanolamide, 5 parts by weight of the calcium salt of dodecylbenzenesulfonic acid and 5 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

III. 20 parts by weight of compound No. 11 are dissolved in a mixture which consists of 40 parts by weight of cyclohexanone, 30 parts by weight of isobutanol, 20 parts by weight of the adduct of 7 moles of ethylene oxide with 1 mole of isooctylphenol and 10 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

IV. 20 parts by weight of compound No. 11 are dissolved in a mixture which consists of 25 parts by weight of cyclohexanol, 65 parts by weight of a mineral oil fraction boiling within the range from 210° to 280° C. and 10 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

V. 20 parts by weight of compound No. 4 are thoroughly mixed with 3 parts by weight of the sodium salt of diisobutylnaphthalene-α-sulfonic acid, 17 parts by weight of the sodium salt of a ligninsulfonic acid from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

VI. 3 parts by weight of compound No. 7 are mixed with 97 parts by weight of finely divided kaolin. A dust which contains 3% by weight of the active ingredient is obtained in this manner.

VII. 30 parts by weight of compound No. 9 are thoroughly mixed with a mixture of 92 parts by weight of silica gel powder and 8 parts by weight of paraffin oil, which was sprayed onto the surface of this silica gel. A formulation of the active ingredient having good adhesion is obtained in this manner.

VIII. 20 parts by weight of compound No. 8 are thoroughly mixed with 2 parts of the calcium salt of dodecylbenzenesulfonic acid, 8 parts of fatty alcohol polyglycol ether, 2 parts of the sodium salt of a phenolsulfonic acid/urea/formaldehyde condensate and 68 parts of a paraffinic mineral oil. A stable oily dispersion is obtained.

IX. 10 parts by weight of compound No. 10 are thoroughly mixed with 4 parts by weight of the sodium salt of diisobutylnaphthalene-2-sulfonic acid, 20 parts by weight of the sodium salt of a ligninsulfonic acid from a sulfite waste liquor, 38 parts by weight of silica gel and 38 parts by weight of kaolin, and the mixture is milled in a hammer mill. By finely distributing the mixture in 10,000 parts by weight of water, a spray liquor which contains 0.1% by weight of the active ingredient is obtained.

The action and the rate of action can be promoted, for example, by additives which increase the effect, such as organic solvents, wetting agents and oils. This permits a reduction in the application rate of the actual active ingredient.

The agents are fed to the plants mainly by spraying the foliage. Application may be effected, for example, using water as the carrier, by conventional spraying methods with about 100–1,000 l/ha of spray liquor. The agents can be used by the low volume and ultralow volume methods as well as being applied in the form of microgranules.

The novel agents can be used in application rates of from 0.1 to 3,000, preferably from 0.5 to 1,000, in particular from 1 to 500, g/ha.

The agents can be used either alone or as a mixture with other agents or with other active ingredients. If necessary, other defoliants, desiccants, crop protection agents or pesticides may be added, depending on the intended use.

We have also found that mixtures of the novel agents, for example with the active ingredients (A.)-(C.) stated below, lead to even better control of the undesirable resprouting of plants after desiccation or defoliation in cotton. The successful defoliation is maintained or even enhanced:

(A) Herbicidal active ingredients from the group consisting of
a. Chloroacetanilides, such as 2-chloro-N-(2,6-dimethylphenyl)-N-(1H-pyrazol-1-ylmethyl)-acetamide (common name: metazachlor), described in German Laid Open Application DOS 2,648,008,
b. Substituted quinoline-8-carboxylic acids, such as 3,7-dichloroquinoline-8-carboxylic acid, described in EP-A-104 389, and 3-methyl-7-chloroquinoline-8carboxylic acid, described in EP-A-60 429,
c. Cyclohexenone derivatives, such as 2-[(1-ethoximino)-butyl]-5-[2-(ethylthio)-propyl]-3-hydroxy-2-cyclohexen-1-one (common name: sethoxydim), described in German Laid-Open Application DOS 2,822,304, and 2-[1-(ethoximino)-butyl]-3-hydroxy-5-(2H-tetrahydrothiopyran-3-yl)-2-cyclohexen-1-one (common name: cycloxydim), described in German Laid-Open Application DOS 3,121,355,
d. Phenoxyalkanecarboxylic acids, such as (4-chloro-2-methylphenoxy)-acetic acid, e. 3-Isopropyl-1H-2,1,3-benzothiadiazin-4(3H)-one 2,2dioxide, described in German Laid-Open Application DOS 1,542,836 (Bentazon ®), f. Dinitroanilines, such as N-(1-ethylpropyl)-3,4-dimethyl-2,6-dinitroaniline, described in German Laid-Open Application DOS 2,241,408, g. Imidazolinones, eg. 2-[4,5-dihydro-4-methyl-4-(1-methylethyl)-5-oxo-1H-imidazol-2-yl]-3-quinolinecarboxylic acid (Scepter ®), h. 3,4,5,6-Tetrahydrophthalimides, such as N-[5-(ethyl α-chloroacrylate)-4-chlorophenyl]-3,4,5,6-tetrahydrophthalimide, described in EP-A 0 240 659, and i. Diphenyl ethers, such as the Na salt of 5-[2-chloro-4-(trifluoromethyl)-phenoxy]-2-nitrobenzoate (Blazer ®), described in DE-A 23 11 638, or ethoxycarbonylmethyl 5-[2-chloro-4-(trifluoromethyl)-phenoxy]-2-nitrobenzoate (Superblazer ®).

Preferred components of the mixture are:
2-methyl-6-ethylethoxymethyl-2-chloroacetanilide
2-methyl-6-ethyl-N-(methoxy-1-methylethyl)-2-chloroacetanilide
2,6-dimethyl-N-(1H-pyrazol-1-ylmethyl)-2-chloroacetanilide
2,6-diethyl-N-(methoxymethyl)-2-chloroacetanilide
3-methyl-7-chloroq-uinoline-8-carboxylic acid (salts, esters)
3,7-dichloroquinoline-8-carboxylic acid (salts, esters)
2-[(1-ethoximino)-butyl]-5-[2-(ethylthio)-propyl]-3-hydroxy-2-cyclohexan-1-one (salts)
2-[(1-trans-chloroallyloximino)-butyl]-5-[2-(ethylthio)-propyl]-3-hydroxy-2-cyclohexan-1-one (salts)
2-[(1-trans-chloroallyloximino)-propyl]-5-[2-(ethylthio)propyl]-3-hydroxy-2-cyclohexan-1-one (salts)
2-[(1-ethoximino)-butyl]-5-[2H-tetrahydrothiopyran-3-yl]-3-hydroxy-2-cyclohexan-1-one (salts)
2-[(1-ethoximino)-propyl]-5-(2,4,6-trimethylphenyl)-3-hydroxy-2-cyclohexan-1-one (salts)
2-methyl-4-chlorophenoxyacetic acid (salts, esters, amides)
2-[2-methyl-4-chlorophenoxy]-propionic acid (salts, esters, amides)
35 4-[2-methyl-4-chlorophenoxy]-butyric acid (salts, esters, amides)
4-[2,4-dichlorophenoxy]-butyric acid (salts, esters, amides)
2-[2,4-dichlorophenoxy]-propionic acid (salts, esters, amides)
2,4-dichlorophenoxyacetic acid (salts, esters, amides)
3,5,6-trichloropyrid-2-yloxyacetic acid (salts, esters, amides)
3-(1-methylethyl)-1H-2,1,3-benzothiadiazin-4-(3H)-one 2,2-dioxide (salts)
3-(1-methylethyl)-1-cyano-2,1,3-benzothiadiazin-4-(3H)-one 2,2-dioxide (salts)
N-(1-ethylpropyl)-3,4-dimethyl-2,6-dinitroaniline
2-[4,5-dihydro-4-methyl-4-(1-methylethyl)-5-oxo-1H-imidazol-2-yl]-3-quinolinecarboxylic acid
N-[5-(ethyl α-chloroacrylate)-4-chlorophenyl]-3,4,5,6-tetrahydrophthalimide
Sodium 5-[2-chloro-4-(trifluoromethyl)-phenoxy]-2-nitrobenzoate
ethoxycarbonylmethyl 5-[2-chloro-4-(trifluoromethyl)-phenoxy]-2-nitrobenzoate
5-[2-chloro-4-(trifluoromethyl)-phenoxy]-2-nitrobenzoic acid methylsulfonylamide (B) Defoliants and desiccants, as mentioned, for example, in Cathey, G. W. (1986), Physiology of defoliation in cotton production, in Cotton Physiology (J. R. Mauney, J. McD. Stewart, eds.) The Cotton Foundation Reference Book Series No. 1, Chapter 14, 143–153, and from. Morgan, P. W. (1985), Chemical manipulation of abscission and desiccation, in Agricultural Chemicals of the Future (J. L. Hilton, ed.) BARC Symposium 8, 61–74, Rowman & Allanheld, Totowa.

a. Urea derivatives, such as N-phenyl-N'-1,2,3-thiadiazol-5-ylurea, disclosed in German Laid-Open Applications DOS 2,506,690 and DOS 2,619,861, N-phenyl-N'-1,3,4-thiadiazol-2-ylurea, described in German Laid-Open Application DOS 3,612,830, or N-phenyl-N'-2-chloropyrid-3-ylurea, described in German Laid-Open Application DOS 2,843,722, b. (2-Chloroethyl)-phosphonic acid (Ethrel ®), c. S,S,S-Tributyl phosphorotrithioate and S,S,S-tributyl phosphorotrithioite, d. 2,3-Dihydro-5,6-dimethyl-1,4-dithiine 1,1,4,4-tetraoxide (Harvade ®), e. Salts of N-(phosphonomethyl)-glycine, such as the isopropylammonium salt (Roundup ®), f. Magnesium chlorate and sodium chlorate, g. 1,2-Dihydropyridazine-3,6-dione, h. 7-Oxabicyclo[2.2.1]heptane-2,3-dicarboxylic acid (common name: endothall), i. 6,7-Dihydrodipyridol (1,2-α:2',1'-c)pyridilium ion as the dibromide monohydrate salt (common name: diquat) and 1,1,-dimethyl-4,4,-bipyridinium ion as the dichloride or dimethylsulfate salt (common name: paraquat)

Preferred components of the mixture are:
N-phenyl-N'-2,2,3-thiadiazol-5-ylurea
N-phenyl-N'-1,3,4-thiadiazol-2-ylurea
N-phenyl-N'-2-chloropyrid-3-ylurea
N-(3,4-dichlorophenyl)-N',N'-dimethylurea 2-chloroethylphosphonic acid
S,S,S-tributyl phosphorotrithioate,
S,S,S-tributyl phosphorotrithioite,
2,3-dihydro-5,6-dimethyl-1,4-dithiine 1,1,4,4-tetraoxide
N-(phosphonomethyl)-glycine (salts)
1,2-dihydropyridazine-3,6-dione
perchlorates
7-oxabicyclo[2.2.1]heptane-2,3-dicarboxylic acid (salts, esters, amides)
1,1-ethylene-2,2-bipyridilium dibromide (C) Growth retardants from the group consisting of a. Quaternary ammonium salts from the group consisting of the N,N-dimethylazacycloheptanium salts, N,N-dimethylpiperidinium salts, N,N-dimethylhexahydropyridazinium salts, N,N-dimethyltetrahydropyridazinium salts, N-methylpyridinium salts, N,N-dimethylpyrrolidinium salts and N,N,N-trimethyl-N-2-chloroethylammonium salts, in particular N-2-chloroethyl-N-trimethylammonium chloride (common name: chloromequat chloride) and N,N-dimethylpiperidinium chloride (common name: mepiquat chloride), b. Pyrimidine compounds, as disclosed in US 3 818 009 and in Journal of Plant Growth Regulation 7:27, 1988 (for example those with the common name ancymidol or flurprimidol), c. Pyridine compounds which are disclosed in German Laid-Open Application DOS 3,015,025, d. Norbornadiazetines, as described in German Laid-Open Applications DOS 2,615,878 and DOS 2,742,034, e. Triazole compounds having a growth-regulating action, as described in European Application 88104320.2, in British Crop Protection, Conference Weeds 1982, Vol. 1, BCPC Publications, Croydon, 1982, page 3, in Plant Cell Physiol. 25, 611, in Pestic. Sci. 19, 153, in J. Agron. Crop Sci. 158, 324 or in J. Plant Growth Regul. 4, 181, eg. 1-phenoxy-3-(1H-1,2,4-triazol-1-yl)-4-hydroxy-5,5-dimethylhexane, f. 2-Acyl-3-hydroxycyclohex-2-en-1-ones as described in EP-A-126 713 or 123 001, g. 1-(4-Chlorophenoxy)-3,3-dimethyl-1-[1,2,4-triazol-1-yl]-butan-2-one (common name: triadimefon)

N-[2,4-dimethyl-5-[trifluoromethylsulfonylamino]]-phenylacetamide (common name: mefluidide)

2-Chloro-2',6,-diethyl-N-[methoxymethyl]-acetanilide (common name: alachlor)

S-Ethyl dipropylthiocarbamate (common name: EPTC) Succinic 2,2-dimethylhydrazide (common name: daminozid)

Preferred components of the mixture are:
N,N,N-Trimethyl-N-2-chloroethylammonium salts
N,N-Dimethylpiperidinium salts
N-Methylpyridinium salts
α-Cyclopropyl-α-(4-methoxyphenyl)-5-pyrimidinemethanol α-Cyclopropyl-α-(4-trifluoromethoxyphenyl)-5-pyrimidinemethanol
5-(4-chlorophenyl)-3,4,5,9,10-pentaazatetracyclo-[5.4.1.0$^{2,6}$.0$^{8,11}$]dodeca-3,9-diones
all-cis-8-(4-chlorophenyl)-3,4,8-triazatetracyclo[4.3.1.0.0$^{2,5}$.0$^{7,9}$]$^{dec}$-3-one
Succinic mono-N,N-dimethylhydrazide
Ethyl N,N-dipropylthiocarbamate
N-2,4-Dimethyl-5-(trifluoromethyl)-sulfonylaminophenylacetamide
1-(4-chlorophenoxy)-3,3-dimethyl-1-(1,2,4-triazol-1-yl)-2-butanone
2-propylcarbonyl-5-ethoxycarbonyl-3-hydroxy-2-cyclohexen-1-one
1-(1,2,4-triazol-1-yl)-1-methoxy-2-(2,4-dichlorophenyl)-propan-2-ol
2,2-dimethyl-4-(1,2,4-triazol-1-yl)-6-phenoxyhexan-3-ol
2,2-dimethyl-4-(1,2,4-triazol-1-yl)-5-(4-chlorophenyl)-pentan-3-ol
2,2-dimethyl-4-(1,2,4-triazol-1-yl)-5-(4-chlorophenyl)-pent-4-en-1-ol
2,2-dimethyl-4-(1,2,4-triazol-1-yl)-5-cyclohexylpent-4-en-3-ol
1-(5-methyl-1,3-dioxan-5-yl)-4-(1,2,4-triazol-1-yl)-4-(4-trifluoromethylphenyl)-propen-2-ol Particularly advantageous mixtures are obtained if the compounds I are combined with substituted N-phenyl-3,4,5,6-tetrahydrophthalimides of the formula II

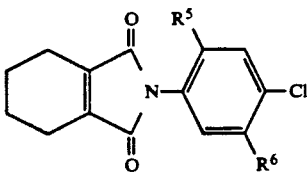

(II)

where R$^5$ is hydrogen, fluorine or chlorine, R$^6$ is a) a radical

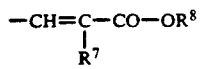

where

R$^7$ is hydrogen, chlorine, bromine, cyano or C$_1$-C$_6$-alkyl and

R$^8$ is hydrogen, C$_1$C$_8$-alkyl, C$_1$-C$_8$-alkenyl, C$_3$- or C$_4$-alkynyl, C$_1$-C$_8$-alkoxyalkyl, C$_1$-C$_8$-alkylthioalkyl, phenyl-C$_1$-C$_8$-alkyl or C$_3$-C$_6$-cycloalkyl, or b) a radical

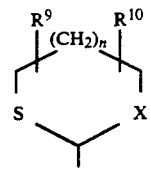

where
X is oxygen or sulfur,
n is 0 or 1,
R$^9$ is hydrogen or C$_1$-C$_4$-alkyl which may be substituted by hydroxyl, halogen, cyano, mercapto, C$_1$-C$_4$-alkoxy, C$_1$-C$_4$- alkylthio, C$_1$-C$_4$-alkylcarbonyloxy or C$_1$-C$_4$-alkoxycarbonyl-C$_1$-C$_4$-alkylthio, and
R$^{10}$ is hydrogen or C$_1$-C$_3$-alkyl, or
c) a radical OR$^{11}$, where
R$^{11}$ is C$_1$-C$_4$-alkyl, C$_3$- or C$_4$-alkenyl, C$_3$- or C$_4$-alkynyl, C$_1$-C$_4$-alkylcarbonyl, C$_1$-C$_4$-alkoxycarbonyl-C$_1$-C$_4$-alkyl and in particular tetrahydrofurfuryl, dihydropyranylmethyl, dihydrothiopyranylmethyl, tetrahydropyranylmethyl or tetrahydrothiopyranylmethyl.

Mixtures of the compounds I with N-phenyl-3,4,5,6-tetrahydrophthalimides of the formula IIa, where R$^5$ has the abovementioned meanings and R$^6$ is the radical

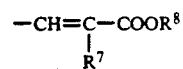

where R$^7$ and R$^8$ have the abovementioned meanings and, particularly preferably, R$^7$, is chlorine or bromine and R$^8$ is C$_1$-C$_4$-alkyl, e.g. ethyl or methyl, are particularly preferred.

The preparation of N-substituted tetrahydrophthalimides II is described in detail in DE-A 39 05 916. They are obtainable from 3,4,5,6-tetrahydrophthalic anhydride and correspondingly substituted aniline derivatives, which can be obtained by reducing the corresponding nitro compounds. As a rule, the reaction is carried out in an inert solvent at from 20° to 200° C., preferably from 40° to 150° C. Examples of suitable solvents are lower alkanecarboxylic acids, such as glacial acetic acid or propionic acid, or aprotic solvents, such as toluene or xylene, in the presence of acidic catalysts, for example aromatic sulfonic acids. The preparation of the compounds II and IIa can be carried out similarly to the methods described in EP-A 240 659, 300 387, 300 398, 236 916, 313 963, 319 791 and 320 677 or DE-A-31 09 035 and 35 33 440 or GB-A 2 071 100.

The phenylsulfonyl- or hetarylsulfonylureas I and the tetrahydrophthalimides II can be used in weight ratios of from 100 : 1 to 1 : 100, weight ratios of from 50 : 1 to 1 : 50 are preferably used in the mixtures. Use Examples The following were used as comparative agents A 6,7-Dihydrodipyridol (1,2-α2',1'-c)pyridilium as the dibromide monohydrate salt (diquat), B 2-chloroethylphosphonic acid (Ethrel ®),
C    N-phenyl-N'-(1,2,3-thiadiazol-5-yl)-urea (Dropp ®),
D

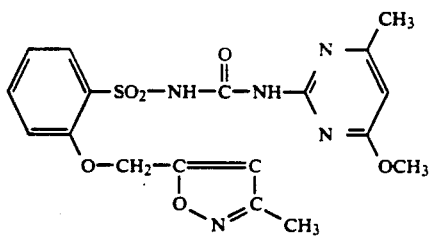

disclosed in DE-A 34 13 565 and
E the synergistic agent

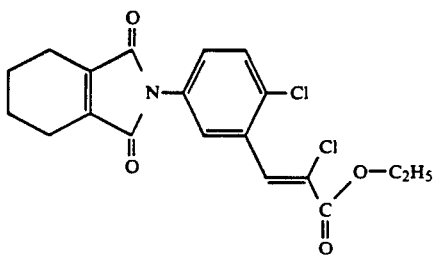

disclosed in EP-A 0 240 659.

The active ingredients were used in the form of their ready-formulated commercial products or were formulated as stated below:

10 parts by weight of each of the compounds No. 8 and D are thoroughly mixed with 4 parts by weight of the sodium salt of diisobutylnaphthalene-α-sulfonic acid, 20 parts by weight of the sodium salt of a ligninsulfonic acid from a sulfite waste liquor, 38 parts by weight of silica gel and 38 parts by weight of kaolin, and the mixture is milled in a hammer mill. By finely distributing the mixture in 10,000 parts by weight of water, a spray liquor which contains 0.1% by weight of the active ingredient is obtained.

Compound E was formulated according to formulation example III, page 7.

The amount of water in the formulations converts to 1,000 l/ha.

The test plants used were young 6-leaved cotton plants (without dicotyledons) of the variety Stonevill 825, which were grown under greenhouse conditions (relative humidity from 50 to 70%).

USE EXAMPLE 1

The leaves of the cotton plants were treated to run-off with aqueous formulations (with the addition of 0.15% by weight, based on the spray liquor, of the fatty alcohol alkoxylate Plurafac ® LF 700) of the stated active ingredients. 10 days after application of the active ingredient, the number of dropped leaves and the degree of defoliation in % were determined. In the case of the untreated control plants, no leaf fall occurred. Resprouting of the plants was determined after 18 days (day/night temperature 25/18° C.).

| Agent, containing active ingredient No. | Converted application rate [kg/ha] | Defoliation [%] | Resprouting |
|---|---|---|---|
| 1 | 0.016 | 90* | 0 |
| 2 | 0.016 | 100* | 0 |
| 10 | 0.016 | 83 | 0 |
| 3 | 0.016 | 67 | + |
| 4 | 0.016 | 90 | 0 |
| 13 | 0.016 | 68 | +++ |
| 8 | 0.016 | 91 | ++ |
| Comparative agent A | 0.250 | 65* | +++ |
| Comparative agent B | 0.250 | 46 | +++ |

*Desiccation (withering) symptoms detectable on the leaves
Rating:
+++ pronounced,
+ slight resprouting;
0 no resprouting The results of Use Example 1 show that, even at a low application rate, the novel agents lead to defoliation of the plants and efficiently suppress resprouting. They are clearly superior to the comparative

USE EXAMPLE 2

Leaves of the cotton plants were treated to run-off with aqueous formulations of the stated active ingredients (with the addition of 0.15% by weight, based on the spray liquor, of the fatty alcohol alkoxylate Plurafac ® LF 700). 9 days after application of the active ingredient, the number of dropped leaves and the degree of defoliation were determined. In the case of the untreated control plants, no leaf fall occurred night temperature 25/18° C.).

| Agent, containing active ingredient No. | Converted application rate [kg/ha] | Defoliation [%] |
|---|---|---|
| 1 | 0.032 | 80* |
| 2 | 0.032 | 91* |
| 10 | 0.032 | 82 |
| 4 | 0.032 | 82 |
| 13 | 0.032 | 45 |
| 8 | 0.032 | 97* |
| 7 | 0.032 | 84 |
| 9 | 0.032 | 47 |
| Comparative agent A | 0.032 | 0 |
|  | 0.1 | 0 |
| Comparative agent B | 0.032 | 0 |
|  | 0.1 | 0 |
| Comparative agent C | 0.032 | 34 |
| Comparative agent D | 0.032 | 0 |

*Desiccation (withering) symptoms detectable on the leaves

The results of Use Example 2 show that the novel agents have a clearly superior action as defoliants compared with the commercial active ingredients A, B and C and the phenylsulfonylurea D.

USE EXAMPLE 3

Leaves of the cotton plants were treated to run-off with aqueous formulations of the stated active ingredients (with the addition of 0.15% by weight, based on the spray liquor, of the fatty alcohol alkoxylate Plurafac ® LF 700). 13 days after application of the active ingredient, the number of dropped leaves and the degree of defoliation were determined. In the case of the untreated control plants, no leaf fall occurred. Resprouting of the plants was determined after 21 days (day/night temperature 26/18° C.)

| Agent, containing active ingredient No. | Converted application rate [kg/ha] | Defoliation [%] | Resprouting |
|---|---|---|---|
| 10 | 0.016 | 80 | ++ |
| 10 + E | 0.016 + 0.125 | 94 | + |
| E | 0.125 | 77 | ++++ |

Rating:

++++ pronounced,

+ slight resprouting:

0 no resprouting

The results show that N-phenyl-3,4,5,6-tetrahydrophthalimide E increases the activity of the thiophenesulfonylurea 10 as a defoliant in cotton and greatly inhibits resprouting of the plants.

We claim:

1. An agent for defoliating cotton plants, containing, in addition to conventional additives, a phenylsulfonyl- or hetarylsulfonylurea of the formula I $$A-SO_2-NH-\underset{O}{\overset{\|}{C}}-\underset{R^2}{N}-\underset{N}{\overset{N}{\underset{\|}{=}}}\underset{R^4}{\overset{R^3}{\underset{Z}{=}}}$$

where A is an aromatic or heteroaromatic radical of the structure A-1 to A-5

A-1, A-2

A-3, A-4

A-5 in which $R^1$ is chlorine, carbomethoxy, carboethoxy, 2-chloroethoxy or 2-methoxyethoxy, $R^2$ is hydrogen or methyl, $R^3$ is methyl, methoxy, difluoromethoxy, chlorine or methylamino, $R^4$ is methyl, methoxy, difluoromethoxy or ethoxy and Z is CH or N, or the alkali metal or alkaline earth metal salts of the compound I.

2. A composition for defoliating cotton plants, containing, in addition to conventional additives, a phenylsulfonylurea I as defined in claim 1, where A is a phenyl radical A-1 substituted by $R^1$,
$R^2$ is hydrogen,
$R^3$ is methyl or methoxy,
$R^4$ is chlorine, methyl or methoxy and
Z is CH or N.

3. A composition for defoliating cotton, containing, in addition to conventional additives, a thiophenesulfonylurea I as defined in claim 1, where
A is the radical A-5,
$R^2$ is hydrogen,
$R^3$ is methyl,
$R^4$ is methoxy and
Z is nitrogen.

4. A method for defoliating cotton, wherein an amount, having a defoliant effect, of an agent as defined in claim 1 is allowed to act on cotton plants.

5. A composition for defoliating cotton, containing, in addition to conventional additives, a thiophenesulfonylurea I as defined in claim 1, where
A is the radical A-5,
$R^2$ is hydrogen,
$R^3$ is methyl,
$R^4$ is methoxy and
Z is CH.

6. A method for defoliating cotton, wherein an amount, having a defoliant effect, of an agent as claimed in claim 2 is allowed to act on cotton plants.

7. A method for defoliating cotton, wherein an amount, having a defoliant effect, of an agent as claimed in claim 3 is allowed to act on cotton plants.

UNITED STATES PATENT AND TRADEMARK OFFICE
CERTIFICATE OF CORRECTION

PATENT NO. : 5,087,282
DATED : Feb. 11, 1992
INVENTOR(S) : GROSSMAN et al.

It is certified that error appears in the above-identified patent and that said Letters Patent is hereby corrected as shown below:

On the title page:

In the title, delete "SULFONYLURA" and insert --SULFONYLUREA--

In the Abstract, on the third line below chemical structure, delete "Rhu 2" and insert --$R^2$--.

Signed and Sealed this

Twenty-seventh Day of April, 1993

Attest:

MICHAEL K. KIRK

*Attesting Officer*     *Acting Commissioner of Patents and Trademarks*